US005681933A

United States Patent [19]
Auron et al.

[11] Patent Number: 5,681,933
[45] Date of Patent: Oct. 28, 1997

[54] ANTIBODIES TO IL-1β

[75] Inventors: Philip E. Auron, Middlesex County; Charles A. Dinarello, Suffolk County; Andrew C. Webb, Norfolk County; Alexander Rich, Middlesex County; Sheldon M. Wolff, Norfolk County, all of Mass.

[73] Assignees: New England Med. Center Hospitals; Tufts College, both of Boston; Wellesley College, Wellesley; Mass. Inst. of Technology, Cambridge, all of Mass.

[21] Appl. No.: 71,031

[22] Filed: Jun. 1, 1993

Related U.S. Application Data

[63] Continuation of Ser. No. 880,476, May 6, 1992, abandoned, which is a continuation of Ser. No. 557,279, Aug. 30, 1990, abandoned, which is a division of Ser. No. 185,731, Apr. 25, 1988, Pat. No. 5,510,462, which is a division of Ser. No. 4,319, Jan. 8, 1987, Pat. No. 4,766,069, which is a continuation of Ser. No. 611,669, May 18, 1984, abandoned.

[51] Int. Cl.$^6$ .................................................. C07K 16/24
[52] U.S. Cl. ........................ 530/389.2; 530/387.1; 530/388.23; 530/389.1
[58] Field of Search .......................... 530/389.2, 387.1, 530/389.1, 388.23

[56] References Cited

U.S. PATENT DOCUMENTS

| | | | |
|---|---|---|---|
| 4,772,685 | 9/1988 | Schmidt et al. | 530/326 |
| 4,898,818 | 2/1990 | Nakai et al. | 435/69.1 |
| 4,935,343 | 6/1990 | Allison et al. | 424/85.2 |

FOREIGN PATENT DOCUMENTS

| | | |
|---|---|---|
| 0165654 | 12/1985 | European Pat. Off. . |
| 0188864 | 7/1986 | European Pat. Off. . |
| 0188920 | 7/1986 | European Pat. Off. . |
| 0245052 | 11/1987 | European Pat. Off. . |
| 0267611 | 5/1988 | European Pat. Off. . |

OTHER PUBLICATIONS

Sevier et al., Clin Chem. 27:1797–1806, 1981.
Dinarello et al., PNAS USA 74:4624–4627, 1977.
Stadler et al, Prog. Cancer. Res. Ther., 1981, 20, pp. 69–76.
Boraschi et al, Prog. Leukocyte Biol 8, 1988, pp. 197–202.
Wunderlich et al, Prog Leukocyte Biol 8, 1988, pp. 383–385.
Kack et al; *J. Exp. Medicine* 163, 1986, pp. 463–468.
Nizel et al. *J. Immunol* 131, 1983, pp. 1834–1837.
Auron, Philip E., Andrew C. Webb, Lanny J. Rosenwasser, Steven F. Mucci, Alexander Rich, Sheldon M. Wolff, and Charles A. Dinarello (1984) "Nucleotide sequence of humanmonocyte interleukin 1 precursor cDNA" Proc. Natl. Acad. Sci. USA 81:7907–7911.
Stadler, Beda M., Suznne F. Dougherty, Charles Center, Joost J. Oppenheim (1982) "Monoclonal antibodies against the interleukins" Chemical Abstracts 96:484 (abstract No. 33132e).
Lachman, Lawrence B. (1983) "Human interleukin 1: purification and properties" 99:405 (abstract No. 36951u).
Auron, P.E., A.C. Webb, L.J. Rosenwasser, S.F. Mucci, A. Rich, S.M. Wolff, C.A. Dinarello (1984) "Molecular cloning of human interleukin–1 cDNA" Biological Abstracts vol. 28 (abstract No. 54236).

*Primary Examiner*—Toni R. Scheiner
*Attorney, Agent, or Firm*—Saliwanchik, Lloyd & Saliwanchik

[57] ABSTRACT

The subject invention concerns a nucleic acid comprising a nucleotide sequence encoding human interleukin-1 (IL-1), and fragments thereof, and the polypeptides and peptides obtained. Specifically, the subject invention comprises the cloning of a cDNA synthesized by reverse transcription of poly(A)RNA isolated from adherent human monocytes stimulated with bacterial endotoxin. The subject invention further concerns antibodies that are immunoreactive with human IL-1β proteins. Human IL-1 is useful to induce the production of IL-2 by activated T-cells; it also acts on B-cells and NK-cells.

5 Claims, 3 Drawing Sheets

Fig. 2A

```
                                                                       M  A  E  V  P  K  L  A↓S  E  M  M12
ACAAACCTTTCGAGGCAAAAAGGCTGCTCTGGAATTCTCTTCAGCCAATCTTCAAGTGTCTGAAGCAGCCATGGCAGAAGTACTAAGCTCGCCAGTGAAATGA
         10        20        30        40        50        60        70        80        90       100       110       120

A  T  Y  S  G  N  E  D  D  L  F  F  E  A  D  G  P  K  Q  M  K  C  S  F  Q  D  L  D  L  C  P  L  D  G  G  I  Q  L  R  I52
TGGCTTATTACAGTGGCAATGAGGATGACTTGTTCTTTGAAGCTGATGGGCCCTAAACAGATGAAGTGCTCTCCTTCCAGGACCTGGACCTCTGCCCTCTGGATGGGGGCATCCAGCTACGAA
       130       140       150       160       170       180       190       200       210       220       230       240

S  D  H  H  Y  S  K  G  F  R  Q  A  A  S  V  V  V  A  M  D  K  L  R  K  M  L  V  P  C  P  Q  T  F  Q  E  N  D  L  S  T92
TCTCCGACCACCACTACAGCAAGGGCTTCAGGCAGGCCGCGTCAGTTGTGTGGCCATGGACAAGCTGAGGAAGATGCTGGTTCCCTGCCCACAGACCTTCCAGGAGAATGACCTGAGCA
       250       260       270       280       290       300       310       320       330       340       350       360

F  F  F  I  F  E  E  P  I  F  F  D  T  W  D  N  E  A  Y  V  H  D  A  P  V  R  S  L  N  C  T  L  R  D  S  Q  Q  K132
CCTTCTTTCCCTCATCTTTGAAGAAGAACCTATCTTCTTCGACACATGGGATAACGAGGCTTATGTGCACGATGCACCTGTACGATCACTGAACTGCACGTCCGGGACTCACAGCAAA
       370       380       390       400       410       420       430       440       450       460       470       480

S  L  V  M  S  G  P  Y  E  L  K  A  L  H  L  Q  G  Q  D  M  E  Q  Q  V  V  F  S  M  S  F  V  Q  G  E  E  S  N  D  K  I172
AAAGCTTGGTGATGTCTGGTCCATATGAACTGAAGGCTCTCCACCTCCAGGGACAAGATATGGAGCAACAAGTGGTGTTCTCCATGTCCTTTGTACAAGGAGAAAGTAATGACAAAA
       490       500       510       520       530       540       550       560       570       580       590       600

P  V  A  L  G  L  K  E  K  N  L  Y  L  S  C  V  L  K  D  D  K  P  T  L  Q  L  E  S  V  D  P  K  N  Y  P  K  K  K↓M  E212
TACCTGTGGCCTTGGGCCTCAAGGAAAAGAATCTGTACCTGTCCTGCGTGTTGAAGGATGATAAGCCCACTCTACAGCTGGAGAGTGTAGATCCCAAAAATTACCCAAAGAAGAAGATGG
       610       620       630       640       650       660       670       680       690       700       710       720

K  R  F  V  F  N  K  I  E  I  N  N  K  L  E  F  E  S  A  Q  F  P  N  W  Y  I  S  T  S  Q  A  E  N  M  P  V  F  L  G252
AAAAGCGATTTGTCTTCAACAAGATAGAAATCAATAACAAGCTGGAATTTGAGTCTGCCCAGTTCCCCAACTGGTACATCAGCACCTCTCAAGCAGAAAACATGCCCGTCTTCCTGGGAG
       730       740       750       760       770       780       790       800       810       820       830       840
```

Fig. 2B

ANTIBODIES TO IL-1β

This application is a continuation of Ser. No. 07/880,476, filed May 6, 1992, now abandoned; which is a continuation of Ser. No. 07/557,279, filed Aug. 30, 1990, now abandoned; which is a division of Ser. No. 07/185,731, filed Apr. 25, 1988, now U.S. Pat. No. 5,510,462; which is a division of Ser. No. 07/004,319, filed Jan. 8, 1987, now U.S. Pat. No. 4,766,069; which is a continuation of Ser. No. 06/611,669, filed May 18, 1984, now abandoned.

Financial assistance was provided by the National Institutes of Health (NIH) in NIH grants A115614, A117833, and CA04186.

BACKGROUND OF THE INVENTION

It is well established that mononuclear phagocytes are required for antigen recognition and lymphocyte activation, and that they play a vital role in the immune response of the host to infectious, inflammatory and malignant disease. Several aspects of immunological function and host response to infection and injury are attributable to various proteins and other mediators released from stimulated mononuclear phagocytes (Dinarello, C. A. Rev. Inf. Dis. 6, 51–95 [1984]). These include leukocytic pyrogen (LP), a mediator of fever; leukocytic endogenous mediator (LEM), an inducer of several components of the acute phase response; lymphocyte activating factor (LAF), which augments both lymphocyte proliferation and lymphokine production; and mononuclear cell factor (MCF), which induces prostaglandin $E_2$ and collagenase synthesis in synovial cells. It has been demonstrated that LP and LAF activity co-purify and share common physical characteristics (Rosenwasser, L. J., Dinarello, C. A., and Rosenthal, A. S. J. Exp. Med. 150, 709–714 [1979]; Rosenwasser, L. J. and Dinarello, C. A. Cell. Immunol. 63, 134–142 [1981]; Murphy, P. A., Simon, P. L., and Willoughby, W. F. J. Immunol. 124, 2498–2501 [1980]). Similarly there is evidence that LP and LEM are closely related if not the same molecule (Kampschmidt, R. F. in The Physiologic and Metacolic Responses of the Host [eds M. C. Powanda and P. G. Canonico] 55–74 [Elsevier/North-Holland, Amsterdam, 1981]) and furthermore that LAF and MCF seem to be identical (Mizel, S. B., Dayer, J. M., Krane, S. M., and Mergenhagen, S. E. Proc. Natl. Acad. Sci. USA 78, 2474–2477 [1979]). The term interleukin-1 (IL-1) is now used to describe these varied biological activities, although it is presently unclear whether IL-1 represents a single substance or a family of related molecules. Prior to the subject invention the art had no knowledge of the nucleotide sequence coding for human IL-1. Though the art was aware of general cloning procedures, there is no teaching or suggestion in the prior art which could be used to identify and clone the nucleotide sequence coding for human IL-1.

BRIEF SUMMARY OF THE INVENTION

The subject invention concerns a nucleic acid comprising a nucleotide sequence coding for human IL-1, and fragments thereof, and to the polypeptides and peptides obtained. Specifically, the subject invention comprises the cloning of a cDNA synthesized by reverse transcription of poly(A) RNA isolated from adherent human monocytes stimulated with bacterial endotoxin. Injection of hybrid-selected poly (A)RNA into Xenopus laevis oocytes directed the synthesis of biologically active LAF. The nucleotide sequence, as well as immunoprecipitation of poly(A)RNA-directed reticulocyte translation, suggests that human IL-1 is initially synthesized as a precursor peptide with a molecular weight of 30,747.

The subject invention further concerns antibodies to human IL-1β and fragments thereof, as well as a process for producing such antibodies by immunizing an animal.

BRIEF DESCRIPTION OF THE DRAWINGS

FIGS. 2a and 2b show the consensus nucleotide sequence of human monocyte IL-1 cDNA and the predicted amino acid sequence of the protein in single letter code.

DETAILED DESCRIPTION OF THE INVENTION

Figure 1:
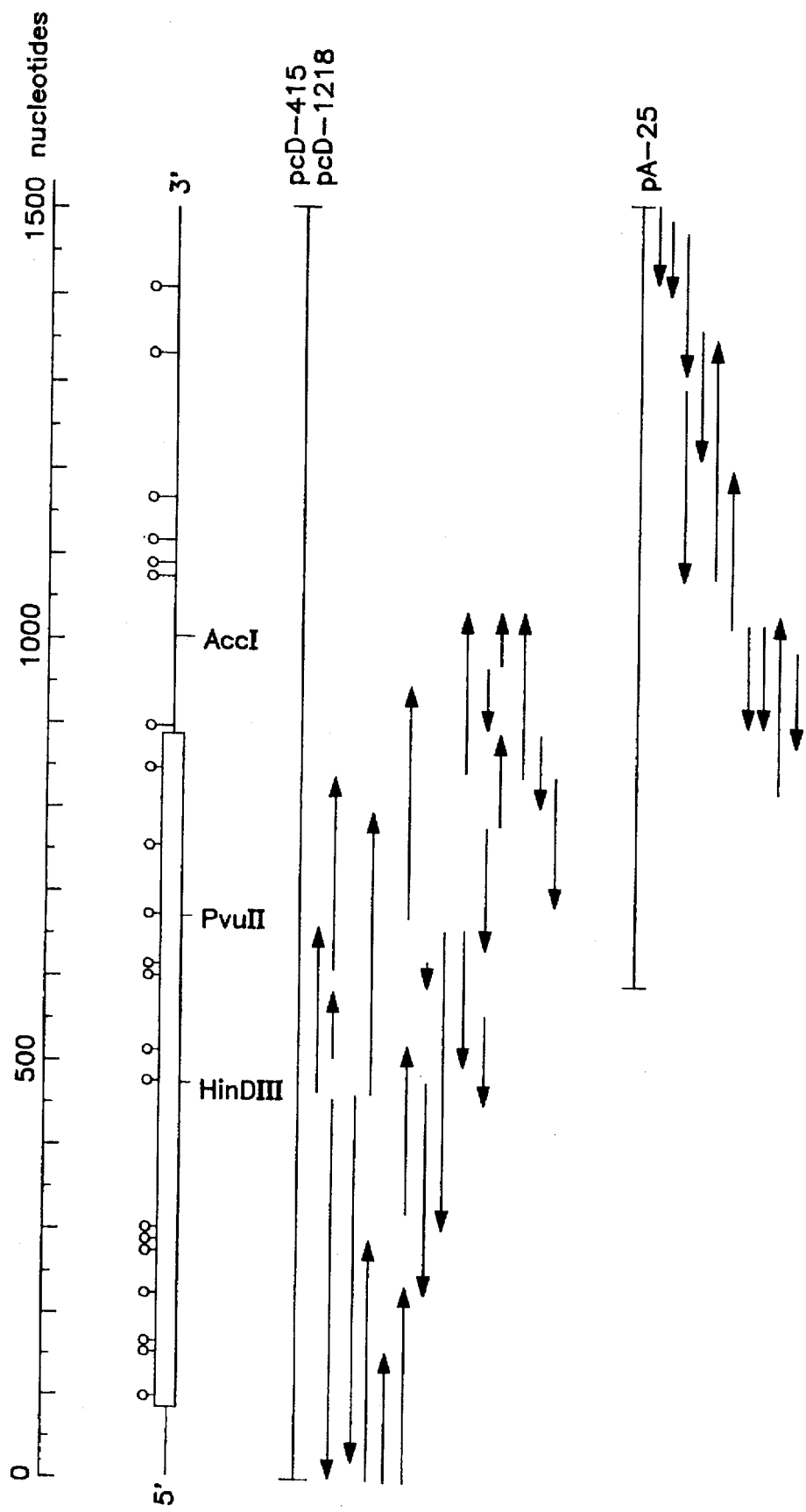
FIG. 1 shows a schematic summary of the strategy used for the nucleotide sequence determination.

Monocytes were separated from lymphocytes in human peripheral blood mononuclear cells by using adherence to glass surfaces. The adherent monolayers (80–90% monocytes, as judged by microscopic examination of phagocytized staphylococcal particles) were stimulated with endotoxin. Total cellular mucleic acid was extracted from the adherent cell population, purified by centrifugation through CsC1 (Chirgwin, J. M., Przybyla, A. E., MacDonald, R. J., and Rutter, W. J. Biochemistry 18, 5294–5299 [1979]), and enriched for poly(A)RNA by passage over oligo dT cellulose (Bantle, J. A., Maxwell, I. H., and Hahn, W. E. Analytical Biochem. 72, 413–427 [1976]).

Aliquots of poly(A)RNA were assayed for protein synthesis by in vitro translation using rabbit reticulocyte lysate containing $^{35}S$-methionine (Pelham, H. R. B. and Jackson, R. J. Eur. J. Biochem. 67, 242–256 [1976]). The translation products were immunoprecipitated using rabbit anti-human IL-1 antiserum (Dinarello, C. A., Renfer, L., and Wolff, S. M. J.Clin. Invest. 60, 465–472 [1977]; Dinarello, C. A., Renfer, L., and Wolff, S. M. Proc. Natl. Acad. Sci. USA 74, 4623–4627 [1977]) and staphylococcal protein A (Kessler, S. W. J. Immunol. 115, 1617–1624 [1975]; Ivarie, R. D. and Jones, P. P. Analytical Biochem. 97, 24–35 [1979]). The immunoprecipitates were analyzed by SDS-polyacrylamide gel electrophoresis (SDS-PAGE) and autoradiography. The reticulocyte translation of stimulated monocyte-derived poly (A)RNA exhibits two intense immunoprecipitable bands, migrating with apparent molecular weights of 42,100 and 39,800, which are absent in the unstimulated poly(A)RNA preparation. A third, weaker band, migrating at 28,000 molecular weight also appears to be stimulation-specific. The measurement of the apparent molecular weights of these three proteins as determined by SDS-PAGE seems to be dependent upon the conditions of the electrophoresis. These proteins are represented as the following: 43K band, 42,600±1100; 35K band, 34,678±4800; 26K band, 25,520±3300.

Several poly(A)RNA preparations extracted from 12 h endotoxin-stimulated monocytes were pooled and fractionated by sucrose gradient sedimentation. Each fraction was precipitated with ethanol, translated in a reticulocyte lysate, and analyzed by immunoprecipitation and electrophoresis as described above. RNA from selected fractions was also injected into oocytes. The culture medium from each batch of 20 oocytes was passed over Sephacryl S-200 and the eluted fractions were assayed for LAF activity as described above. It is clear that the majority of the activity clusters around the fractions containing the 35K band (centering on fraction 13).

A cDNA library was prepared from endotoxin-stimulated monocyte poly(A)RNA using the technique and vector described by Okayama and Berg (Molec. Cell. Biol. 2, 161–170 [1982]). This library was screened with $^{32}P$- labelled cDNA probes prepared from stimulated and unstimulated monocyte poly(A)RNA as well as from RNA contained within fraction 12 of the sucrose gradient described above. As a result five cDNA clones representing three different size-classes were isolated on the basis that they were stimulation-specific and strongly related to material contained within fraction 12 of the sucrose gradient.

The cDNAs were used to produce hybrid-selected RNA (Maniatis, T., Fritsch, E. F., and Sambrook, J. *Molecular Cloning: A Laboratory Manual*, Cold Spring Harbor Laboratory, New York [1982]), which was analyzed by in vitro translation similar to that described above. cDNA from several clones hybridized to RNA which can be translated into a protein similar to that seen as a result of the translation of fraction 12 in the sucrose gradient profile.

Clone pA-26 possessed the highest efficiency for hybrid-selection of the target RNA and similarly was associated with the strongest hybridization affinity for the cDNA probes that were used for screening. The cDNA transcript contained in pA-26 was sequenced as shown in FIG. 1, and found to be approximately 920 base pairs in length. The single longest open reading frame for this sequence coded for a protein of ~6,800 molecular weight. Since this did not correspond to the molecular size expected on the basis of the protein found in the reticulocyte translation, it was concluded that the cDNA transcript was not full length. Moreover, when nick-translated pA-26 plasmid DNA was hybridized to a Northern Blot (Rave, N. et al. *Nuc. Acids Res.* 2, 815–825 [1979]; Maniatis, T., Fritsch, E. F., and Sambrook, J. *Molecular Cloning: A Laboratory Manual*, Cold Spring Harbor Laboratory, New York [1982]) of stimulated-monocyte poly(A)RNA, its complementary RNA appeared as a single band approximately 1600 nucleotides in length. Two additional cDNA libraries were constructed from 4-h and 12-h endotoxin-stimulated human monocyte poly(A)RNA using the newer Okayama and Berg procedure (*Molec. Cell. Biol.* 3, 280–289 [1983]). The result was that five 4-h and four 12-h clones hybridized to a DNA probe synthesized from clone pA-26. The cDNA inserts of these clones were of three different size classes. The largest insert (1560 b.p., as determined by agarose gel electrophoresis) was contained in both 12-h (one clone) and 4-h (four clones) libraries.

The 4-h clone pcD-415 hybridizes to an RNA preparation which has IL-1-like (LAF) biological activity when injected into Xenopus laevis oocytes. Furthermore this activity is absent from unstimulated monocyte poly(A)RNA and from hybrid-selected RNA made from the control cDNA 12-h clone pcD-1214, which is structurally unrelated to the pcD-415 clone. The elution position of this material on the Sephacryl S-200 column represents an approximate molecular weight of 20,000. This is in agreement with the molecular size of IL-1 isolated from stimulated monocyte media (Rosenwasser, L. J. and Dinarello, C. A. *Cell. Immunol.* 63, 134–142 [1981]).

From the above, we concluded that the three structurally-related clones pA-26, pcD-415, and pcD-1218 contain cDNA for human monocyte IL-1. These clones were sequenced by the dideoxy chain termination technique following subcloning in various bacteriophage M13 cloning vectors. FIG. 1 is a schematic summary of the strategy used for sequence determination. The top scale indicates the nucleotide positions relative to position 1 of the sequence as detailed in FIGS. 2a and 2b. The line immediately below the scale represents the extent of the sequence. The bold portion of the line delineates the predicted coding region for the IL-1 precursor. Restriction sites utilized in the sequencing procedure are indicated (open circles-Hae III and closed circles—Alu I). The arrows beneath each cDNA clone indicate the direction and extent of gel sequences read from the M13 subclones (Messing, J. and Vieira, J. *Gene* 19, 269–276 [1982]) (mp8 and mp9) using the dideoxy terminator method (Sanger, F., Nicklen, S., and Coulson, A. R. *Proc. Natl. Acad. Sci. USA* 74, 5463–5467 [1977]; Biggin, M. D., Gibson, T. J., and Hong, G. F. *Proc. Natl. Acad. Sci. USA* 80, 3963–3965 [1983]).

Figure 2B:
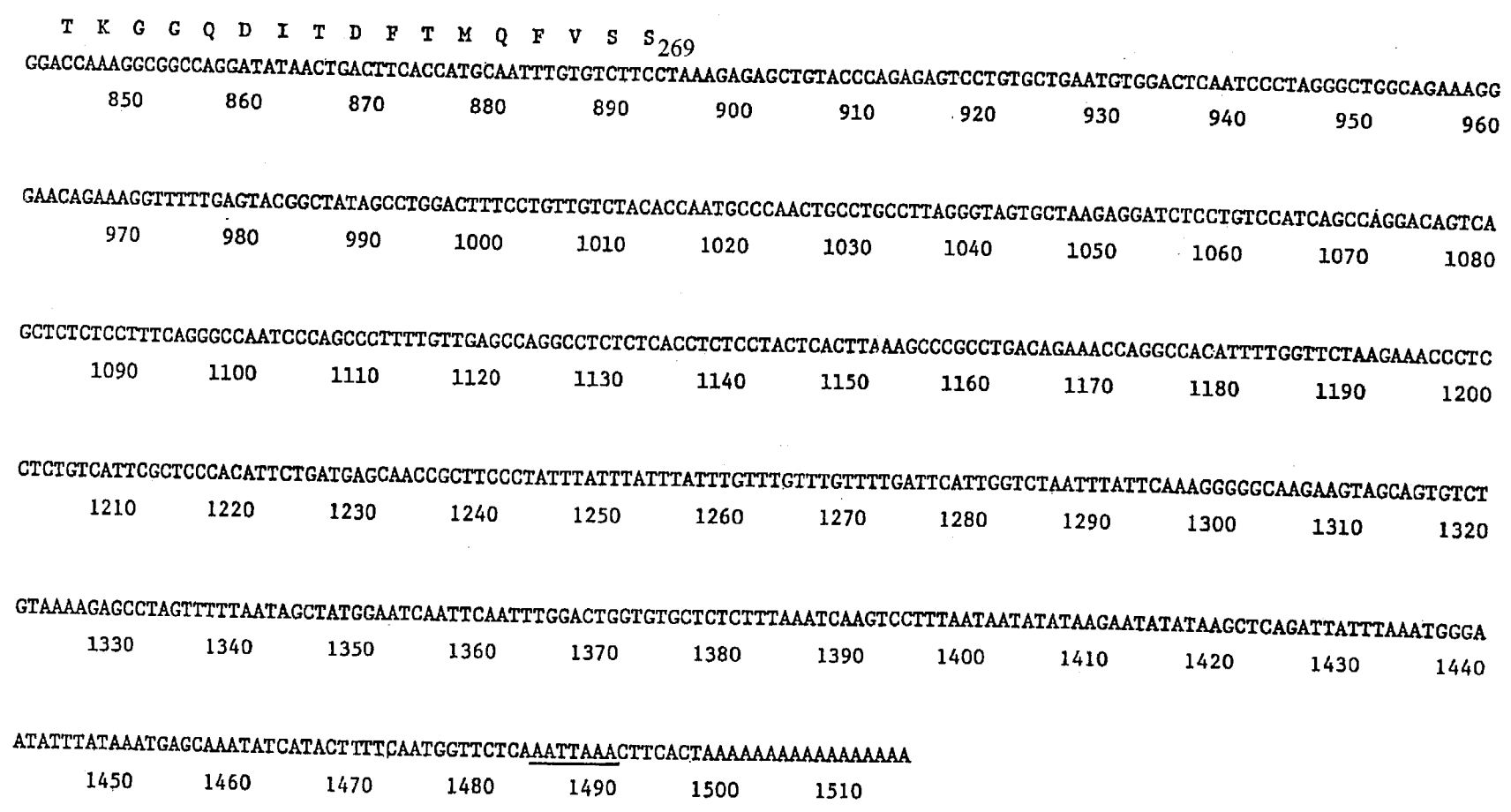

The consensus nucleotide sequence of human monocyte IL-1 cDNA and the predicted amino acid sequence of the protein is shown in FIGS. 2a and 2b. The apparent coding region corresponds to a molecular weight of 30,747 and is similar in size to the protein translated in reticulocyte lysates, described previously. Nucleotides are numbered with position 1 corresponding to the first nucleotide following the G tails resulting from cloning with the Okayama-Berg system. The amino acid residues are indicated by one-letter symbols and the cannonical eukaryotic translational initiation consensus sequence (Kozak, M. *Nuc. Acids Res.* 12, 857–872 [1984]; Kozak, M. *Nature* 308, 241–246 [1984]) is underlined. Boxed nucleotides represent a potential glycosylation-site (Rubinstein, M. *Biochim. Biophys. Acta* 695, 5–16 [1982]) and a potential polyadenylation signal (Proudfoot, N. J. and Brownlee, G. G. *Nature* 263, 211 [1976]).

As disclosed above, our criteria for IL-1 identification are stringent, relying on data both from immunoprecipitation and biological assay of in vitro translation products. The polypeptide(s) in question must be stimulation specfic, immunoprecipitable, and demonstrate biological activity. Significantly, using these same criteria, little or no activity was observed in association with poly(A)RNA isolated from monocytes which were not stimulated by endotoxin. The reticulocyte lysate translation of poly(A)RNA extracted from stimulated cells reveals a major stimulation-specific polypeptide with a molecular weight which is similar to that predicted by the cDNA sequence. This corresponds to one of the two molecular weight species of IL-1 activity previously found in the medium of human monocytes following stimulation, as well as IL-1 recovered from human synovial fluid. In the subject disclosure, biological activity from micro-injected Xenopus oocytes and the activity found in stimulated monocyte media, co-elute from Sephacryl S-200 with an apparent molecular weight of 20,000, corresponding to the species reported by most investigators. This monocyte-derived protein can be isolated from endotoxin-stimulated monocytes incubated with $^{35}$S-methionine in culture yielding a biologically-active, radiolabelled molecule which migrates as a 22,000 molecular weight species when analyzed on the same SDS-PAGE system disclosed herein.

The cDNA nucleotide sequence suggests that the initial translation product is larger than the protein usually associated with IL-1 activity. We suggest, therefore, that a proteolytic "cascade" processes IL-1 following synthesis and/or release from stimulated monocytes. Throughout this proteolysis the molecule remains biologically active. Data derived from in vitro pulse-chase experiments support a precursor-product relationship between a large protein (approximately 31,000 molecular weight) and a series of smaller species which cross-react with our anti-serum. An arrow in FIGS. 2a and 2b located between $Ala_8$ and $Ser_9$ marks a potential signal sequence cleavage site somewhat similar to that predicted for Interleukin-2 (Taniguchi, T., Matsui, H., Fujita, T., Takaoa, C., Kashima, N., Yoshimoto, R., and Hamuro, J. *Nature* 302, 305–310 [1983]). A second arrow located between $Lys_{210}$ and $Met_{211}$ locates a potential cleavage site much like that described by Kronenberg et al. (Kronenberg, H. M., McDevitt, B. E., Majzoub, J. A., Sharp, P. A., Potts, J. T., and Rich, A. *Proc. Natl. Acad. Sci. USA* 76, 4981–4985 [1979]) for the cleavage of the pro-sequence from bovine proparathyroid hormone. These two potential cleavage sites delineate a putative peptide of 23,000 molecular weight, which is in reasonable agreement with the 15,000 to 20,000 size range reported by most investigators for the primary IL-1 activity.

Clone (plasmid) pcD-415, which contains the cDNA for human monocyte IL-1 was deposited in an *E. coli* HB101 host in the permanent collection of the Northern Regional Research Laboratory, U.S. Department of Agriculture, Peoria, Ill., USA, on Apr. 27, 1984. The culture was assigned the accession number NRRL B-15770 by the repository. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

Recombinant plasmid pcD-415 can be isolated from its *E. coli* HB101 host by well-known procedures, e.g., using cleared lysate-isopycnic density gradient procedures, and the like.

Also, it is within the skill of those in the art to vary the conditions disclosed herein for cloning the nucleotide sequence coding for human IL-1.

The cloned human IL-1 gene can be used to detect related DNAs in the human genome by well-known probe techniques. Further, unlimited amounts of nucleic acid comprising a nucleotide sequence coding human IL-1 can be made by the cloned human IL-1 gene of the subject invention. Still further, the IL-1 produced by the cloned gene of the subject invention can be used to induce the production of IL-2 by activating T-cells—IL-2 stimulates the T-cells to proliferate. As reported in *Science*, 221, 1362–1364, "Researchers from NIAID and the Food and Drug Administration (FDA), using a test tube assay, have recently found that interleukin-2 improved the function of T cells from six AIDS patients" (p. 1362).

In vitro, IL-1 activates neutrophils to degranulate and is also chemotactic. The most studied effects of IL-1 are on lymphocytes. IL-1 acts on B-cells, T-cells, as disclosed above, and NK-cells. On B-cells, IL-1 acts in conjunction with other B-cell activators as an adjuvant. It boosts B-cell proliferation and immunoglobulin synthesis (Lipsky, P. E., Thompson, P. A., Rosenwasser, L. J., Dinarello, C. A. *J. Immunol.* 130, 2708 [1983]; Falkoff, R. J. M., Muraguchi A. Hong, J. X., Butler, J. L., Dinarello, C. A., Fauci, A. S. *J. Immunol.* 131, 801 [1983]). On T-cells, IL-1 acts as a co-factor for T-cells to produce various lymphokines. IL-2 and leukocyte migration inhibitory factor have been studied as lymphokines which require a signal from IL-1 in the absence of monocytes or antigen presenting accessory cells (Mizel, S. B. *Immunol. Rev.* 63, 51 [1982]).

Another aspect of IL-1 is its inflammatory properties. IL-1 has been isolated from the synovial fluid of patients with various forms of arthritis (Wood, D. D., Ihrie, E. J., Dinarello, C. A., Cohen, P. L. *Arthr. Rheumat.* 26, 975 [1983]), and its ability to increase collagenase and prostaglandin $E_2$ from synovial cells implicates IL-1 in the pathogenesis of several arthritides. In muscle tissue, IL-1 also induces prostaglandin $E_2$ but this leads to increased lysosomal protease activity and increases protein breakdown from muscle tissue (Baracos, V., Rodemann H. P., Dinarello, C. A., Goldberg, A. L. *New Engl. J. Med.* 308, 553 [1983]). In brain tissue, IL-1 also increases prostaglandin E and this plays a key role in the development of the febrile response (Dinarello, C. A. IN: *Lymphokines*, 4, ED). More recent research involves IL-1 in the induction of sleep (Kreuger, J. M., Walter, J., Dinarello, C. A., Wolff, S. M., Chedid, L. *Am. J. Physiol.* in press) and in fibroblast proliferation and collagen synthesis (Schmidt, J. A., Mizel, S. B., Cohen, D., Green, I. *J. Immunol.* 128, 2177 [1982]).

Because of its central role as a mediator of host immunological and defense functions, detection of IL-1 in different disease states is likely to shed light on certain pathological processes, and levels of IL-1 may indicate the severity of certain disease states where this is masked by special drugs. There is evidence that IL-1 production is reduced in human subjects with certain cancers (Hofmann, M. K., Pollack, S. IN: *Interleukins, Lymphokines and Cytokines*. E D Oppenheim, J. J., Cohen, S. Academic Press, 707–14 [1983]) and malnutrition (Keenan, R. A., Moldawer, L. L., Yang, R. D., Kawamura, I., Blackburn, G. L., Bistrian, B. R. *J. Lab. Clin. Med.* 100, 844 [1982]) and this has been supported by studies in animal models.

Use of IL-1 as an immunological reagent in humans or animals is likely because of its ability to stimulate T- and B-cells and increase immunoglobulin synthesis. In fact, IL-1 appears to be an excellent candidate for the body's endogenous adjuvant. Thus, it is possible to use IL-1 or parts of the IL-1 molecule in certain immunogens.

A further aspect of the claimed invention concerns antibodies to human IL-1β that are raised by immunizing an animal with the precusor IL-1β protein or fragments thereof.

The following examples are illustrative of the process and products of the subject invention but are not to be construed as limiting. All percentages are by weight and all solvent mixture proportions are by volume unless otherwise noted.

EXAMPLE 1

Preparation of Poly(A)RNA

Human mononuclear cells ($4-6\times10^9$) were isolated from Ficoll-Hypaque gradient separation of plateletphoresis by-products. Cells were washed 4× in 0.9% NaCl at 600× g to remove platelets. Monocytes were plated into flat glass bottles in RPMI (Gibco) containing 1% (v/v) heat-inactivated human AB serum at a density of $1.25\times10^6$ cells/cm$^2$ and allowed to adhere for 1.5 h at 37°. The bottles were then vigorously shaken and the non-adherent population drained and counted. The total number of adherent monocytes was determined by subtracting the non-adhering cells from the total cell count. Replacement (serum-free) RPMI contained 300 ng/ml *E. coli* endotoxin (Difco). After 12 h at 37°, the medium was drained and the adherent monolayer lysed by the addition of 6M guanidinium thiocyanate (Chirgwin, J. M., Przybyla, A. E., MacDonald, R. J. and Rutter, W. J. *Biochemistry* 18, 5294–5299 [1979]). The lysate was frozen at −70° and thawed prior to layering onto CsCl cushions as previously described (See Chirgwin et al. supra). Poly(A)RNA was recovered from the crude nucleic acid pellets by binding to oligo(dT) cellulose twice (Bantle, J. A., Maxwell, I. H., and Hahn, W. E. *Analytical Biochem.* 72, 413–427 [1976]). Total RNA isolated from adherent monocytes ranged from 100–200 µg/10$^9$ cells of which poly(A)RNA consistently represented 5–7%. Preparation of poly(A)RNA from "unstimulated" mononuclear cells by the same procedure but without stimulation or adherence yielded about 500 µg of total RNA/$10^9$ cells of which only 1–2% bound to oligo(dT) cellulose under the conditions used here.

EXAMPLE 2

In Vitro Translation of Poly(A)RNA

Rabbit reticulocyte lysate was prepared, optimized and treated with micrococcal nuclease as described in Pelham, H. R. B. and Jackson, R. J. *Eur. J. Biochem.* 67, 242–256 (1976). Each translation contained 1 µg poly(A)RNA in the presence of 100 µCi $^{35}$S-methionine/ml. After incubation for 1 h at 37°, samples were immunoprecipitated according to the method of Kessler (*J. Immunol.* 115, 1617–1624 [1975]) with some modifications. During pre-clearing, 20 µl of normal rabbit serum (NRS) was added to each sample. This was followed by a 2 h incubation at 4°, after which 100 µl (i.e. 10% (w/v)) protein A (IgGsorb, The Enzyme Center, Boston, Mass.) was added. Samples were allowed to incubate an additional 1 h at room temperature and the IgGsorb was then pelleted by centrifugation in a clinical centrifuge for 10 min at maximum speed. Supernates were transferred to fresh tubes and incubated for 18 h at 4° with 20 µl of rabbit anti-human EP/LAF polyclonal serum (Dinarello, C. A., Renfer, L., and Wolff, S. M. *J. Clin. Invest.* 60, 465–472 [1977]). This antiserum was prepared by 20 monthly immunizations of 15 Kd human EP/LAF obtained after gel filtration (Dinarello, C. A., Goldin, N. P., and Wolff, S. M. *J. Exp. Med.* 139, 1369–1381 [1973]) and has anti-human EP/LAF but no anti-human IL-2 activity. Next, 100 µl IgGsorb was added to each tube, followed by incubation at room temperature for 1 h. IgGsorb was pelleted as described above and the pellet washed by vigorous vortexing with 1 ml aliquots (3×) 0.5% (v/v) Triton X-100. Antigens were then solubilized by the addition of 20 µl electrophoresis buffer containing 6% SDS (Laemli, U. K. *Nature* 227, 680–685 [1970]) and subsequent boiling for 5 min. Again IgGsorb was removed by microfuging for 3 min and the supernatant was then loaded onto a 17.5% polyacrylamide gel (15×17× 0.15 cm) (see Laemli, supra) for electrophoresis at 35 mAmp for 5 h. Gels were treated with fluor (EnHance, NEN), dried and then exposed to photographic film (Kodak, XAR-5) for 24–72 h prior to development.

EXAMPLE 3

Sucrose Gradient Fractionation of Stimulated Monocyte Poly(A)RNA

The sucrose gradient procedure is a modification of that described by Bleackley et al. (*J. Immunol.* 127, 2432–2435 [1981]). Poly(A)RNA (50 µg prepared from stimulated human monocytes) was dissolved in 475 µl of water, heated to 65° for 30 min, quench cooled on ice, and adjusted to: 50 mM Tris-HCl, pH 7.5; 0.1% lithium dodecyl sulfate; and 1 mM EDTA (TLE buffer). Samples were loaded onto isokinetic TLE-sucrose gradients (10–28%) and centrifuged in an SW41 rotor (Beckman) for 19 h (4°) at 35 Krpm. A parallel gradient was run with *E. coli* rRNA as markers. Gradients were fractionated (ISCO Model D) and ethanol precipitated. The RNA pellets were washed 2× in 70% ethanol and then resuspended in 3 µl distilled water. Aliquots of each fraction were translated in rabbit reticulocyte lysate, immunoprecipitated and processed for electrophoresis and autoradiography as described above. In addition, selected fractions were micro-injected into Xenopus oocytes for assessment of biological activity also as described above. Stage V oocytes (Dumont, J. N. *J. Morphol.* 136, 153–180 [1972]) were manually defolliculated in Barth-X medium (Ford, C. C. and Gurdon, J. B. *Embryol. Exp. Morph.* 37, 203–209 [1977]) from the ovaries of adult Xenopus laevis (Nasco, WI) that had been stimulated with human chorionic gonadotropin (Sigma) 1–6 weeks beforehand. These oocytes were each micro-injected with 50 nl of poly(A)RNA solution in sterile distilled water (usually at 1–2 mg/ml). Controls were injected with a similar volume of distilled water only. Microinjected oocytes were incubated individually in round bottom microtiter wells containing 10 µl Barth-X to which was added antibiotics (per ml of culture media: 100 U penicillin; 100 µg streptomycin; 70 µg gentamicin; 2.5 µg amphotericin B) for 40–45 h at 20°. The Barth-X medium from batches of 20 oocytes was pooled and fractionated by gel filtration on a Sephacryl S-200 column (0.6×54 cm) equilibrated in RPMI containing 1% (v/v) heat-inactivated, fetal calf serum. Each fraction (about 1 ml) was placed in 3,500 m.w. cut-off dialysis tubing and concentrated five-fold by submerging in polyethylene glycol 8000 before assaying for LAF activity as reported in Rosenwasser and Dinarello, *Cell. Immunol.* 63, 134–142 (1981).

EXAMPLE 4

Biological Activity of Hybrid-Selected RNA

Oocytes were processed as disclosed in Example 3, except that incubation was for 20 h and oocytes were incubated in microtiter plate wells at a density of 5 oocytes per well in 50 µl Barth-X media. LAF activity was assayed using a modification of the procedure described by Rosenwasser and Dinarello (supra), in which the mouse thymocyte cells were substituted with the D10 cell line described by Kaye, et al. (*J. Exp. Med.* 158, 836–856 [1983]).

EXAMPLE 5 cDNA Clones

Three separate cDNA libraries were used to isolate the three cDNA clones shown in FIG. 1. The first, represented by clone pA-26, was constructed from 12 h endotoxin-stimulated monocyte message using the original Okayama-Berg cloning vector system (*Molec. Cell. Biol.* 2, 161–170 [1982]). The second and third libraries, represented by clones pcD-415 and pcD-1218, are from, respectively, 4 h and 12 h endotoxin-stimulated monocyte message using the newer Okayama-Berg cloning vector system (*Molec. Cell. Biol.* 3, 280–289 [1983]). Libraries were each created using 2 µg of poly(A)RNA. A portion of the first library consisting of approximately 100 clones was screened with three different cDNA probes synthesized from stimulated and unstimulated monocyte poly(A)RNA as well as poly(A) RNA contained in fraction 12 of the sucrose gradient disclosed in Example 3. As a result five clones appeared to be more closely related to the enriched cDNA probe than to the unstimulated-RNA derived probe. The two clones containing the longest nucleotide sequence appeared to be identical on the basis of restriction mapping. One clone, pA-26, was subcloned in M13mp11 following treatment with Bal-31 exonuclease (Wei, C. F., Alianell, G. A., Bencen, G. H., and Gray, H. B. *J. Biol. Chem.* 258, 13506–13512 [1983]). The second and third cDNA libraries were screened with one of the M13 subclones of pA-26 cDNA using a hybridization probe primer (Hu, N. and Messing, J. *Gene* 17, 171 [1982]).

The cDNA transcript can be obtained from the clones in essentially pure form by standard art methods. For example, the cDNA transcript in clone pcD-415 can be clipped from the plasmid by a BamHI-PstI double-digestion (Okayama, H. and Berg, P. *Molec. Cell. Biol.* 3, 280–289 [1983]) and isolated by standard procedures. The essentially pure cDNA thus obtained can be used for subcloning into a different transfer vector.

As is well known in the art, the amino acid sequence of a protein, e.g., IL-1, is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATH | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Try) | TGG |
| Alanine (Ala) | GCL | Arginine (Arg) | WGZ |
| Tyrosine (Tyr) | TAK | Glycine (Gly) | GGL |
| Termination signal | TAJ | | |
| Termination signal | TGA | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T
J=A or G
K=T or C
L=A, T, C or G
M=A, C or T The above shows that the novel amino acid sequence of human IL-1 can be prepared by nucleotide sequences other than that in clone pcD-415. Functionally equivalent nucleotide sequences encoding the novel amino acid sequence of human IL-1, or fragments thereof having IL-1 activity, can be prepared by known synthetic procedures. Accordingly, the subject invention includes such functionally equivalent nucleotide sequences.

The one-letter symbol for the amino acids used in FIGS. 2a and 2b is well known in the art. For convenience, the relationship of the three-letter abbreviation and the one-letter symbol for amino acids is as follows:

Ala A
Arg R
Asn N
Asp D
Cys C
Gln Q
Glu E
Gly G
His H
Ile I
Leu L
Lys K
Met M
Phe F
Pro P
Ser S
Thr T
Trp W
Tyr Y
Val V

Thus, the scope of the subject invention includes not only the specific nucleotide sequence depicted herein, but also all equivalent nucleotide sequences coding for molecules with substantially the same human IL-1 biological activity. The term "equivalent" is being used in its ordinary patent usage here as denoting a nucleotide sequence which performs substantially as the nucleotide sequence identified herein to produce molecules with substantially the same human IL-1 biological activity in essentially the same kind of hosts. Within this definition are subfragments which have human IL-1 biological activity.

It is well within the skill of those in the genetic engineering art to use the nucleotide sequences encoding human IL-1 activity of the subject invention to produce human IL-1 via microbial processes. Fusing the sequences into an expression vector and transforming or transfecting into hosts, either eukaryotic (yeast or mammalian cells) or prokaryotic (bacterial cells), are standard procedures used in producing other well-known proteins, e.g., insulin, interferons, human growth hormone, and the like. Similar procedures, or obvious modifications thereof, can be employed to prepare human IL-1 proteins by microbial means or mammalian tissue-culture technology in accord with the subject invention.

As disclosed previously, the cDNA sequence in FIGS. 2a and 2b discloses, via two arrows, a cDNA sequence which itself codes for a peptide having human IL-1 activity. The isolation of this cDNA sequence is disclosed hereinafter. Upon isolation of the cDNA sequence in its essentially pure form it can be cloned by using the procedures described herein for the entire cDNA sequence coding for human IL-1. Those skilled in the art will appreciate the fact that the cDNA fragment depicted includes substantially biologically (human IL-1 activity) equivalent cDNA sequences, as defined above.

The process for isolating the cDNA fragment is as follows:

Plasmid pcD-415 is digested with Stu I and Xho I restriction endonucleases in order to generate a DNA fragment containing approximately 1370 b.p. of sequence. The sequence of interest (between positions 111–717, FIGS. 2a and 2b) is approximately centered within this fragment (approximately 350 nucleotides from each end). These excess terminal nucleotides can be removed using a time-controlled Bal 31 exonuclease limited digestion (Wei et al. *J. Biol. Chem.* 258, 13506–13512 [1983]). In this way a fragment containing the DNA sequence corresponding to that located between the two arrows in FIGS. 2a and 2b can be generated. Using a combination of techniques which are well known in the art, the resulting Bal 31 fragments can be subcloned and then selected using radioactive probes made from restriction endonuclease digestion fragments made from the original pcD-415 cDNA insert.

We claim:

1. An antibody preparation consisting essentially of antibodies produced by immunizing an animal with essentially pure human precursor IL-1β or an immunogenic fragment thereof.

2. The antibody preparation according to claim 1, wherein said antibodies were originally produced by immunizing an animal with essentially pure precursor IL-1β having the amino acid sequence shown in FIGS. 2a and 2b.

3. An antibody preparation which specifically binds with human precursor IL-1β or an immunogenic fragment thereof.

4. The antibody preparation of claim 1, wherein said immunogenic fragment has a molecular weight of at least about 15 kD.

5. The antibody preparation of claim 4, wherein said immunogenic fragment has a molecular weight from about 15 kD to about 20 kD.

* * * * *